(12) United States Patent
Liu et al.

(10) Patent No.: US 6,407,810 B1
(45) Date of Patent: Jun. 18, 2002

(54) IMAGING SYSTEM

(75) Inventors: Kuo-Ching Liu, Setauket; Shawn Reven, Point Lookout, both of NY (US)

(73) Assignee: Robotic Vision Systems, Inc., Hauppauge, NY (US)

( * ) Notice: Subject to any disclaimer, the term of this patent is extended or adjusted under 35 U.S.C. 154(b) by 0 days.

(21) Appl. No.: 09/522,540

(22) Filed: Mar. 10, 2000

(51) Int. Cl.$^7$ .............................................. G01N 21/00
(52) U.S. Cl. ................................................... 356/237.4
(58) Field of Search ......................... 356/237.1–237.5, 356/417, 416, 311, 394; 382/144, 145, 147, 149, 150, 151, 153; 348/126; 250/458.1, 461.2

(56) References Cited

U.S. PATENT DOCUMENTS

| | | | |
|---|---|---|---|
| 4,772,125 A | * 9/1988 | Yoshimura et al. | 345/237 |
| 5,131,755 A | * 7/1992 | Chadwick et al. | 356/394 |
| 5,278,012 A | * 1/1994 | Yamanaka et al. | 356/237 |
| 5,822,055 A | * 10/1998 | Tsai et al. | 356/394 |
| 6,014,209 A | * 1/2000 | Bishop | 356/237.5 |
| 6,091,488 A | * 7/2000 | Bishop | 356/237.5 |

* cited by examiner

Primary Examiner—Hoa Q. Pham
(74) Attorney, Agent, or Firm—Kenyon & Kenyon

(57) ABSTRACT

A system for imaging an object is described. The system includes a light source for illuminating the object with light, the light from the light source having a first wavelength. The system further includes an image capturing device and a filter device. The filter device is transmissive for light having a wavelength which different than the first wavelength, and reflective for light having the first wavelength, the image capturing device capturing an image of at least a portion of the object using light transmitted through the filter device. The system may further include a dark field illumination system for illuminating the object either simultaneously with the illumination by the first light source, or sequentially with respect to the illumination by the first light source.

38 Claims, 7 Drawing Sheets

IMAGING SYSTEM

FIELD OF THE INVENTION

The present invention relates to an imaging system.

BACKGROUND INFORMATION

Machine vision systems are commonly used in industry for high speed inspection. In particular, these systems are used to obtain digital images of objects in order to determine, with a computer, whether the object is of "acceptable" quality with respect to predetermined specifications.

An example of an application for a machine vision system is inspection of semiconductor chips and semiconductor device packages, both leaded and grid array. In such a system, for leaded packages, automatic inspection using machine vision is carried out, in particular, with respect to defective leads and defects on leads. In a typical system, a number of device packages are imaged while in their carrier tray, and a computer compares the images to device package specifications stored at an earlier time. Many of these systems are fairly good at detecting metallic, highly reflective defects such as slivers or burrs found on leads. However, these conventional systems have difficulty detecting foreign, non-metallic matter, such as fibers and other contamination.

Backlight techniques can be used for leaded packages, but they require handling of each and every device which is potentially damaging to the fragile leads. Backlighting cannot be used on chips or grid array packages.

SUMMARY

According to an example embodiment of the present invention, a system is provided for imaging an object. The system includes a light source for illuminating the object with light, the light from the light source having a first wavelength. The system further includes an image capturing device and a filter device. The filter device is transmissive for light having a wavelength which is different than the first wavelength, and reflective for light at the first wavelength, the image capturing device capturing an image of at least a portion of the object using light transmitted through the filter device. The system may further include a dark field illumination system.

DETAILED DESCRIPTION

Figure 1:
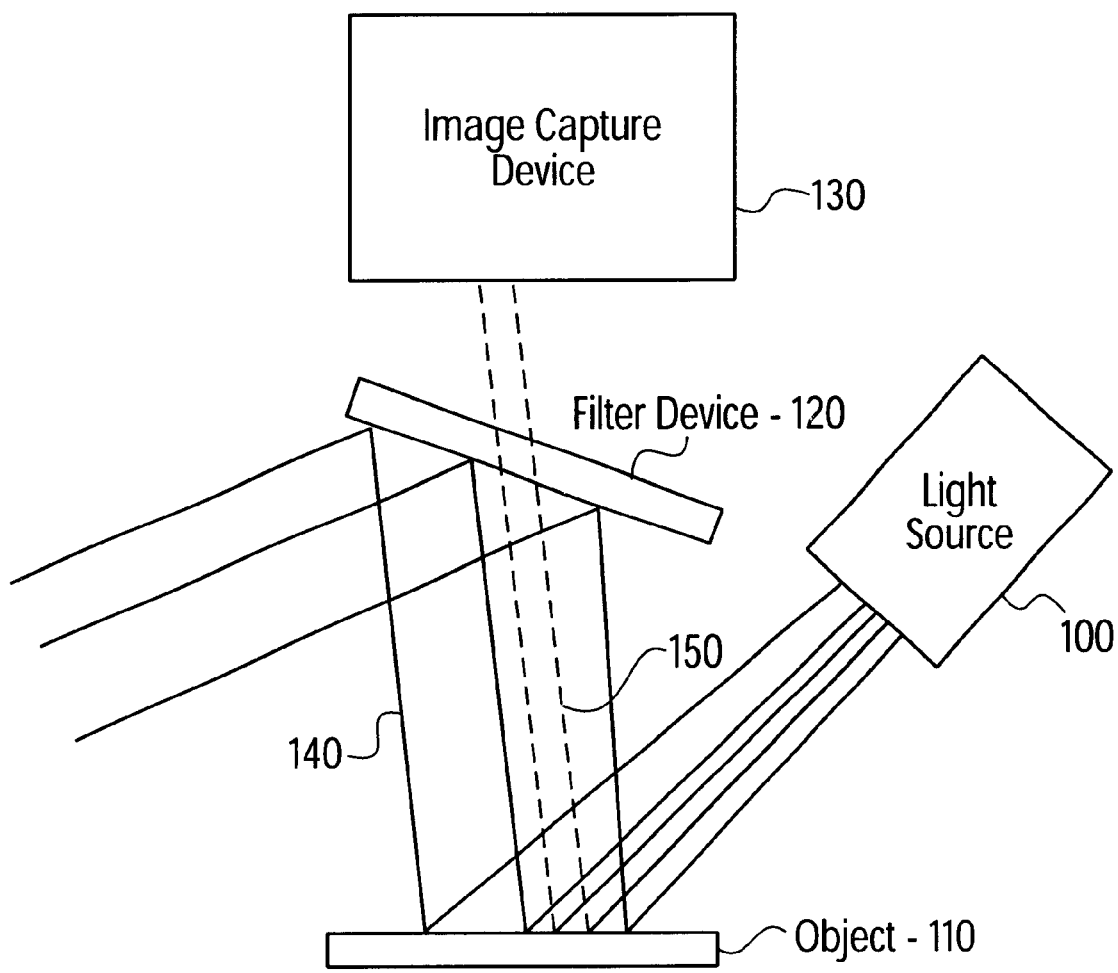
FIG. 1 illustrates a first example system according to the present invention.

FIG. 1 illustrates a first example system according to the present invention. The system includes a light source 100 for illuminating an object 110 with light, the light from the light source 100 having a first wavelength. The system further includes a filter device 120 which, on the one hand, is transmissive for light having a wavelength which is different than first wavelength, and on the other hand, is reflective for light having the first wavelength. An image capturing device 130 captures an image of at least a portion of the object 100 using light transmitted through the filter device.

In one example operation of the first embodiment, the light source 100 illuminates the object 110 with an ultraviolet light. Some of the light which impinges the surface of the object 110, striking, for example, metallic, non-fluorescent portions of the object, is reflected by the object toward the image capture device 130. The filter device 120, configured to reflect, for example, ultraviolet light, directs this reflected light 140 away from the image capture device 130.

Some of the light which impinges the surface of the object 110, striking, for example, non-metallic, fluorescent foreign matter on the object, is absorbed by this matter which then fluoresces as a result. The light 150, for example visible light (e.g., having a wavelength which is longer than the source light), emitted by the object toward the image capture device 130 is transmitted through the filter device 120. The image capture device 130 captures an image of the object using the transmitted light 150.

Figure 2:
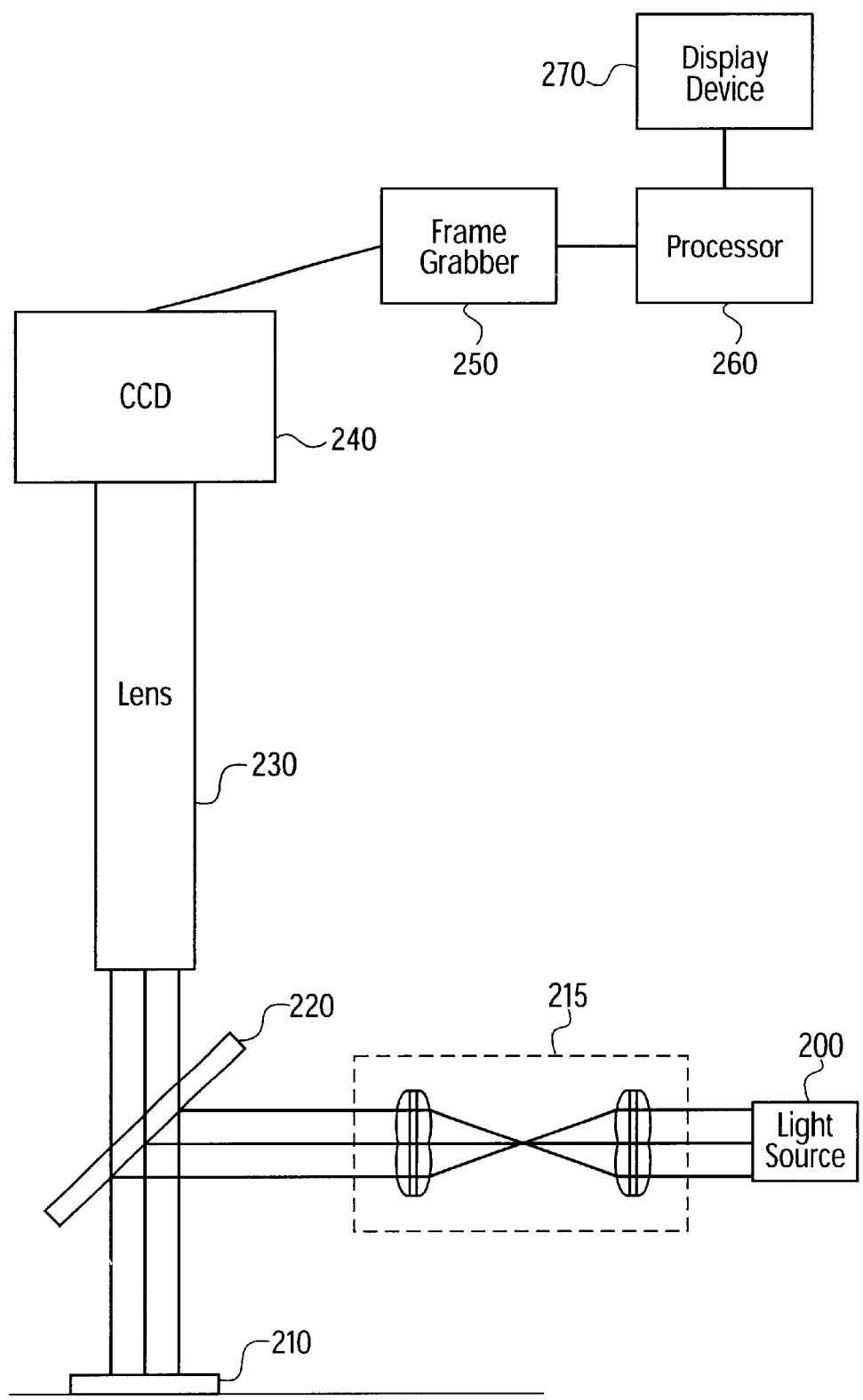
FIG. 2 illustrates a second example system according to the present invention.

FIG. 2 illustrates a second example embodiment of the present invention. This second example embodiment is described in the context of a leaded device inspection system. However, other applications are, of course, possible.

As shown in FIG. 2, a light source 200 is provided to illuminate a leaded device package 210 which may be in its carrier tray with an ultraviolet. light. An excitation light from the light source 200 is transmitted through a lens system 215 to a filter and beam splitter 220 which is configured as, for example, a long pass filter. The filter and beam splitter 220 reflects the light onto the package 210.

Portions of the package 210, for example, the non-fluorescent metal leads and the plastic body, reflect the light impinging thereon. The light reflected from these portions of the device package 210 maintains the same wavelength as the source light, here, ultraviolet. Accordingly, the light reflected from these portions of the device toward the filter and beam splitter 220, is further reflected by the filter and beam splitter 220, i.e., in a direction away from a lens system 230 and charge coupled device (CCD) camera 240.

In accordance with this second example embodiment, the ultraviolet light is absorbed by foreign material on the device package, the foreign material fluorescing as a result. In this example embodiment, the light emitted by the foreign material has a wavelength which is longer than the ultraviolet source light. For example, the emitted light may be in the visible light spectrum. The light that is emitted in the direction of the filter and beam splitter 220 is transmitted through the filter and beam splitter 220.

Light which is transmitted through the filter and beam splitter 220 is directed to the lens system 230 which focuses and/or directs the transmitted light to the CCD 240. The CCD 240 is coupled to a frame grabber 250 and a processor 260, which together capture an image of the object using the transmitted light. A display device 270 may be used to display the captured image to a user of the system. Using the captured image, foreign material on the device package may be identified.

Figure 3:
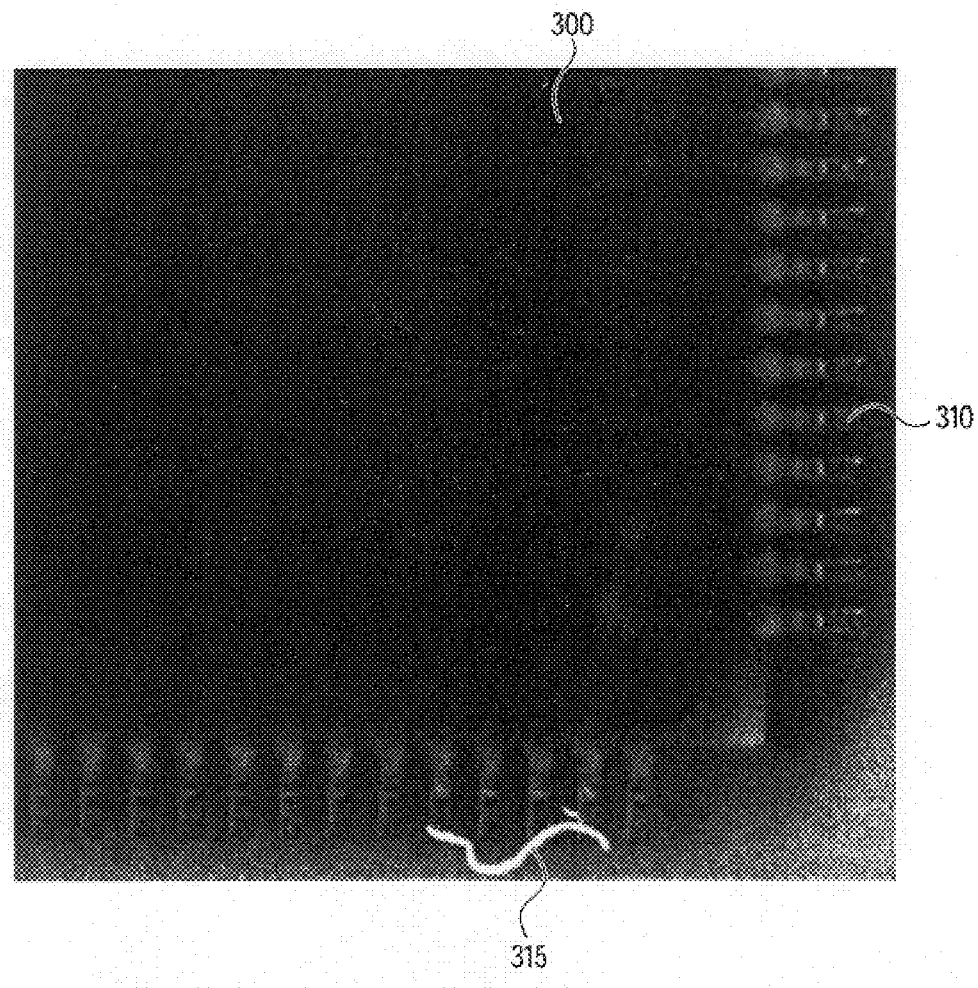
FIG. 3 shows an example of an image captured according to the present invention.

FIG. 3 illustrates an example image of a portion of a package. As shown, the package body 300 and the device leads 310 are barely (if at all) visible. However, a fiber 315 which was adhered to some leads of the device can be clearly seen. Here, the fiber 315 is bright in comparison to the dark background.

Figure 4:
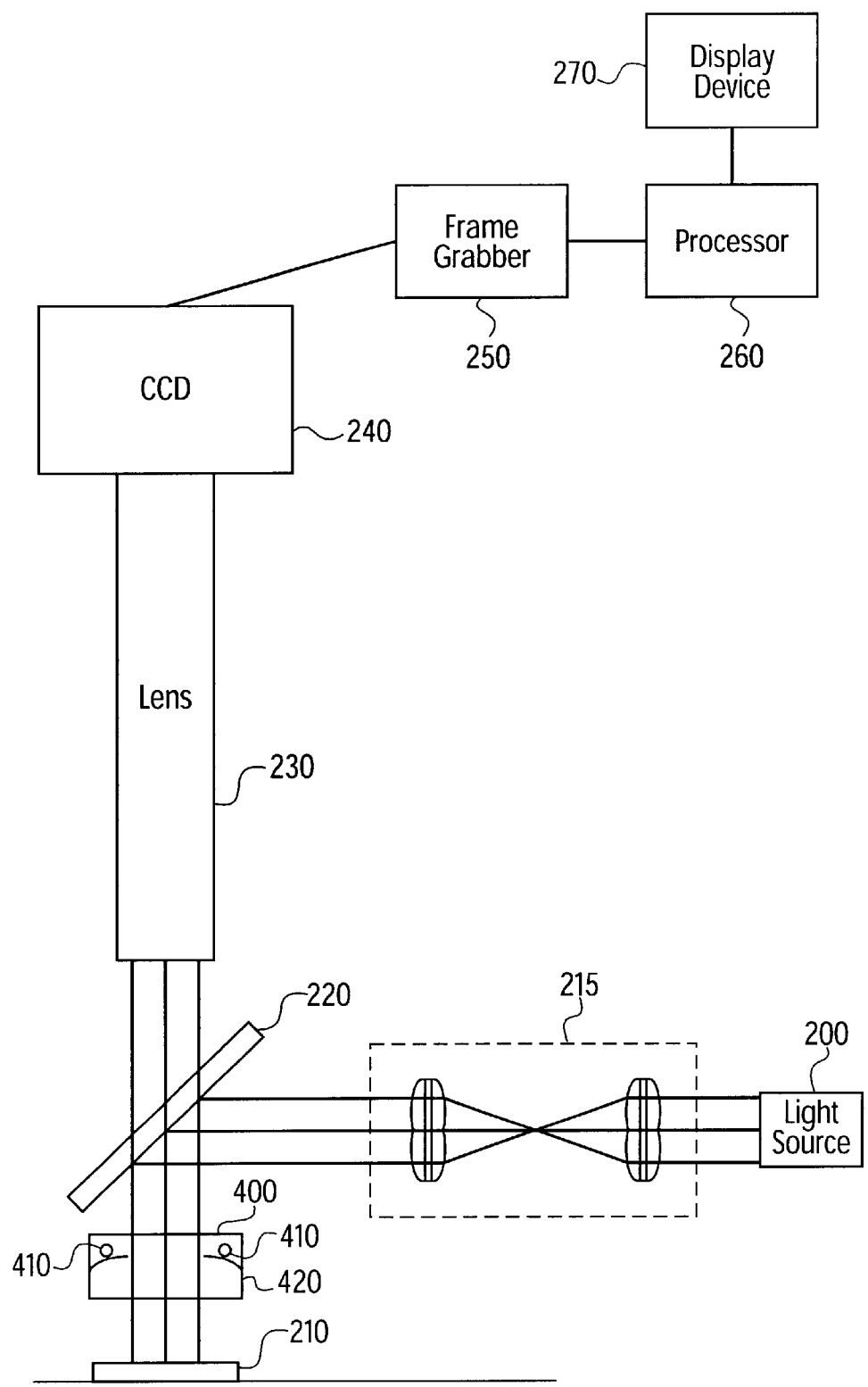
FIG. 4 shows a third example system according to the present invention.

FIG. 4 illustrates a third example embodiment of the present invention. This third example embodiment is an enhancement of the embodiment shown in FIG. 2. In particular, according to this embodiment, a dark field illumination system 400 is added to the embodiment shown in FIG. 2. The dark field illumination 400 may be used for detecting, for example, metallic defects such a sliver or a burr on package leads. Slivers and burrs are manufacturing defects which could cause leads to electrically short to adjacent leads.

As shown in FIG. 4, the dark field illumination system 400 includes a long wavelength light source, such as, for example, a ring light 410, and a diffuser 420 for diffusing the light emitted by the ring light 410. (In the example embodiment, the ring light 410 includes red LEDs.) When the dark field illumination system 400 is actuated, light from the ring light illuminates the package 210. Light impinging, for example, the metallic leads of the package 210 and any slivers or burrs cause at least some of the light to scatter in the direction of the filter and beam splitter 220. This light is transmitted through the filter and beam splitter 220 to the lens 230, onto the CCD 240. The CCD 240 and the frame grabber 250 provide a captured image of the device package 210 to the processor 260 for processing.

In one embodiment, the dark field illumination system 400 and the light source 200 may be operated sequentially. In particular, one image of a first area of the package 210 may be captured using the dark field illumination system 400, and a second image of the first area of the package 210 may be captured using the light source 200. Each of the two images can then be processed and defects detected. The image captured using the dark field illumination system 400 could be processed for metallic defects, while the image captured using the light source 200 could be processed for the non-metallic fluorescent defects.

In another embodiment, the dark field illumination system 400 and the light source 200 may be operated simultaneously. That is, both the dark field illumination system 400 and the light source 200 may be actuated simultaneously, and a single image of an area of the device package 210 may be obtained. In this image, both metallic defects and fluorescent, non-metallic defects would be visible.

Figure 5:
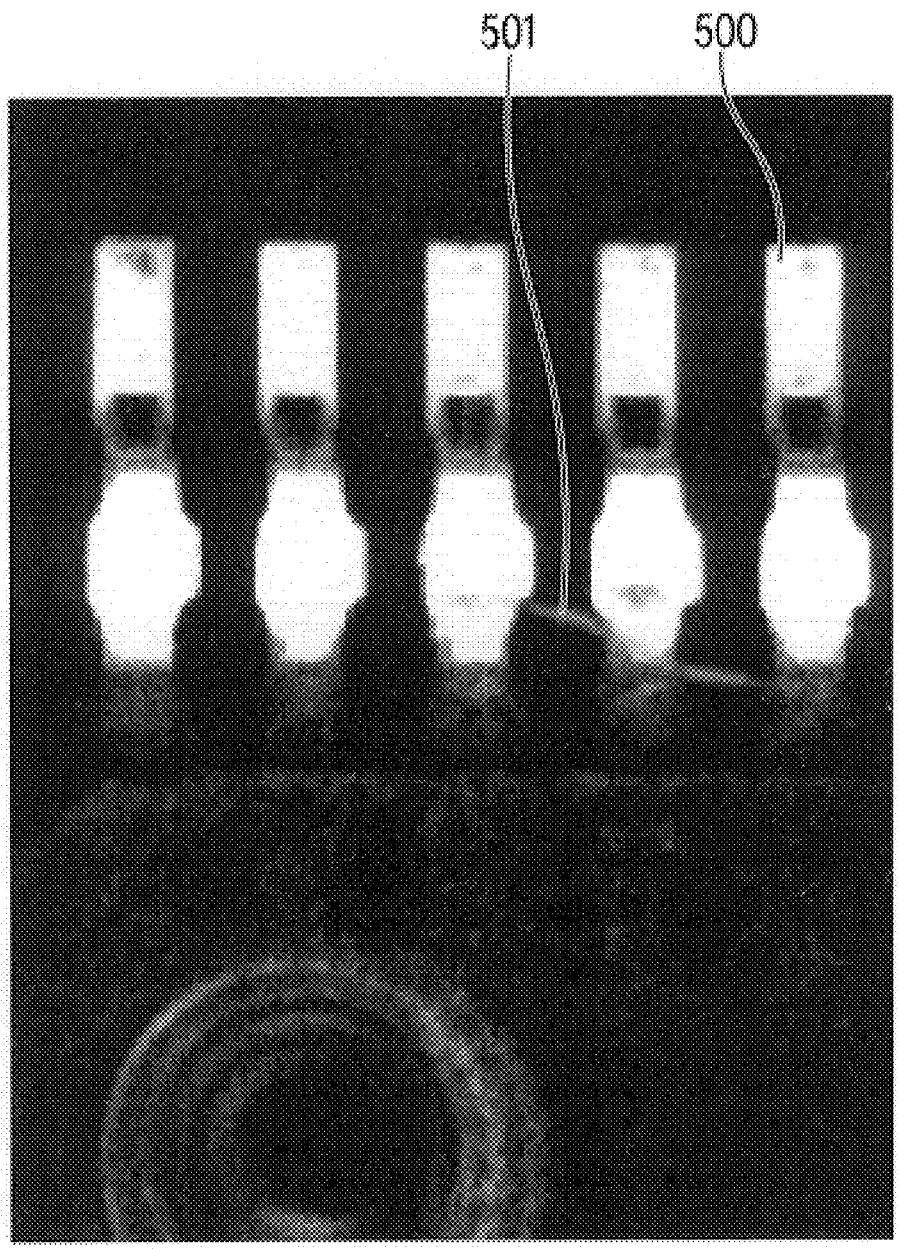
FIG. 5 shows an example of an image captured using the dark field illumination system according to the present invention.

FIG. 5 shows an example of an image captured using the dark field illumination system 400. As shown, the leads 500 of the package and metallic manufacturing defects 501 are clearly visible.

Figure 6:
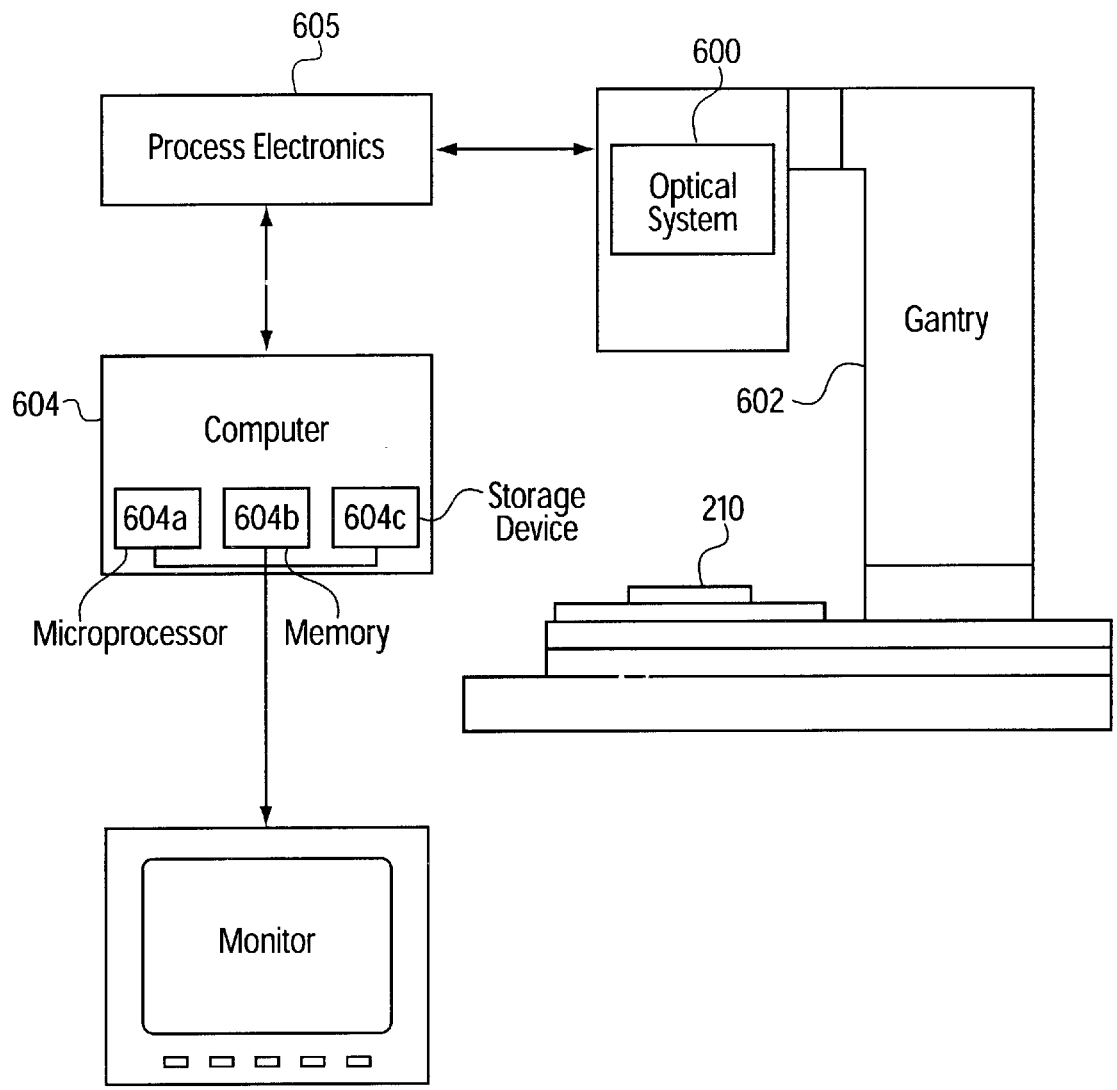
FIG. 6 show a fourth example system according to the present invention.

FIG. 6 shows a third example embodiment of the present invention in schematic form. As illustrated, an optical system 600 is mounted on a gantry 602, and positioned above an object to be measured such as a semiconductor chip or semiconductor device package 210. The chips may still be contained within the wafer upon which they were fabricated or they may be singulated and in carrier trays. Similarly, the semiconductor device packages may be in carrier trays. The optical system 500 may include, for example, one of the optical systems shown in FIG. 2 or FIG. 4, including, e.g., the illumination portions and the filter and beam splitter 220, and the CCD 240. The gantry 602 may include, for example, a motion mechanism (not shown) such as that described in U.S. Pat. No. 5,463,227 issued to Stern et al., expressly incorporated herein by reference, for positioning the optical system 600 to different X-Y positions above the device package 210. The motion mechanism may be controlled by a computer 604 (which includes, for example, a microprocessor 604a, a memory device 604b and a program storage device 604c) to automatically position the device package 210 and the optical system 600 (or a portion of the optical system) relative to each other for image capture. The position of the scanning axis is transmitted by the computer 604 to process electronics 605. (In an alternative embodiment, the optical system 600 remains stationary, and the chip or device package 210 is moved via a translation table automatically controlled by, for example, computer 504). A number of semiconductor device packages may be automatically and sequentially processed using this system, e.g., by automatically moving either the optical system or each of the semiconductors packages at the appropriate time for image capture.

Data collected by the optical system 600 are transmitted as an analog signal to the process electronics 605. The process electronics 605, which includes, for example, digital signal processors (DSPs), digital to analog (D/A) converters, analog to digital (A/D) converters, and input/output (I/O) and communication links, receives and processes the analog data. The processed data is then transmitted to the computer 604 for analysis. The results of the analysis are reported to an operator on output device 606.

Figure 7:
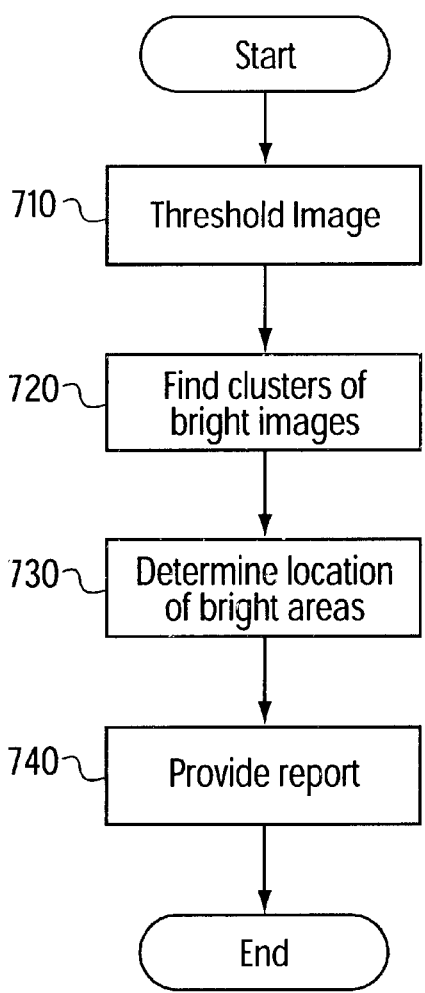
FIG. 7 is a flowchart showing the processing of an image captured using the example system shown in FIG. 2.

FIG. 7 is a flowchart showing the processing of an image captured using the example system shown in FIG. 2. The image obtained is first thresholded (step 710). That is, the intensity value at each X-Y coordinate of the image is compared to a threshold intensity value. If the intensity value is lower than the intensity value, the image portion at that X-Y coordinate is designated "background," and may be set to "0" for example. Everything else is potentially foreign material, and may be set to "1" for example, Next the image is scanned for clusters of "1"s, or bright images (step 720). The location for each cluster found is identified (step 730), and reported (step 740). A package may be rejected based on the number of clusters identified, for example.

Figure 8:
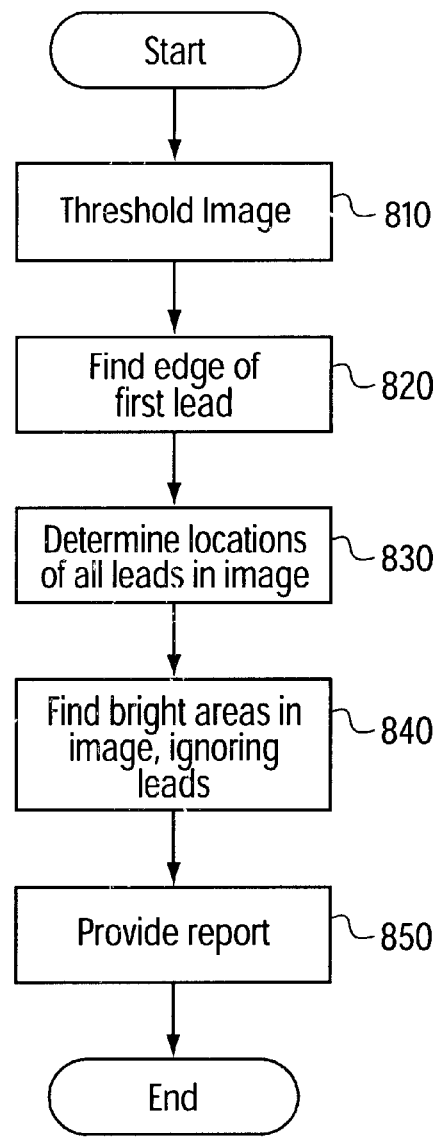
FIG. 8 is a flowchart showing the processing of an image captured using the example system according to FIG. 4.

FIG. 8 is a flowchart showing the processing of an image captured using the example system shown in FIG. 4, in particular, for processing the dark field image, or for processing the image captured using both the dark field illumination system and the light source 200 of FIG. 4.

The image obtained is first thresholded as discussed above in connection with FIG. 7 (step 810). In this image, the leads of the semiconductor device package will be visible, so the image is first searched for visible leads. In particular, the image is searched for an edge of a first lead (step 820). Once the edge of the first lead is found, the remaining leads are located using pre-stored device package specifications, for example (step 830). All of the bright areas in the image can then be located (e.g., by searching for clusters and determining X-Y coordinates), ignoring the leads (step 840). These bright areas may include, for example, images of metal defects such as slivers, and images of fluorescent, non-metallic foreign material (if the light source 200 was used in addition of the dark field illumination system). These areas can then be reported (step 850).

While the present invention has been particularly shown and described with reference to preferred embodiments thereof, it will be understood by those skilled in the art that various changes in form and details may be made therein without departing from the spirit and scope of the invention. For example, it is possible to use an image capture device other than a CCD camera. For example, any type of light sensitive device including, for example, photo sensitive diodes or diode arrays may be used. Also, with respect to the light sources described herein, light at wavelengths other than those described above may be used depending on, for example, the wavelength necessary. for fluorescence excitation or the type of filter arrangement used.

What is claimed is:

1. A system for imaging an object, comprising:
   a light source for illuminating the object with excitation light, the excitation light from the light source having a first wavelength;
   a dark field illumination system for illuminating the object with light having a third wavelength;
   an image capturing device;
   a filter device which is transmissive for fluorescent light emitted by foreign matter on the object and for light at the third wavelength reflected by the object, the fluorescent light being at a second wavelength different from the first wavelength, the filter device further being reflective for light having the first wavelength reflected by the object, the image capturing device positioned to capture an image of at least a portion of the object and the foreign matter on the object using light transmitted through the filter device; and
   a processor actuating the light source and the dark field illumination system to illuminate the object with the excitation light from the light source and light from the dark field illumination simultaneously.

2. The system according to claim 1, wherein light filter device reflects light at the first wavelength away from the image capturing device.

3. The system according to claim 1, wherein the excitation light from the light source is an ultra-violet light.

4. The system according to claim 1, wherein the filter device includes a long pass filter.

5. The system according to claim 1, wherein the filter device is for positioning between the object and the image capturing device.

6. The system according to claim 1, wherein the second wavelength is longer than the first wavelength.

7. The system according to claim 1, wherein the dark field illumination system includes red LEDs.

8. The system according to claim 1, further comprising:
   a positioning device for automatically positioning at least one of: i) the object, and ii) at least a portion of the image capturing device, to a position for capturing the image of the at least the portion of the object and the foreign matter on the object.

9. The system according to claim 1, wherein the foreign matter is non-metallic.

10. The system according to claim 9, wherein the processor is configured to scan the image for defects including the foreign matter on the object.

11. The system according to claim 10, wherein the is processor configured to scan the image for defects including the foreign matter on the object.

12. A system for imaging an object, comprising:
   a light source for illuminating the object with excitation light, the excitation light from the light source having a first wavelength;
   a dark field illumination system for illuminating the object with light having a third wavelength;
   an image capturing device;
   a filter device transmissive for fluorescent light emitted by foreign matter on the object having a second wavelength which is different than the first wavelength and for light having the third wavelength reflected by the object, and reflective for light having the first wavelength reflected by the object, the image capturing device positioned to capture an image of at least a portion of the object and the foreign matter on the object using light transmitted through the filter device;
   a processor automatically actuating the light source and the dark field illumination system sequentially to illuminate the object.

13. The system according to claim 12, wherein the second wavelength is longer than the first wavelength.

14. The system according to claim 12, wherein the light from the light source is an ultra-violet light.

15. The system according to claim 12, wherein the filter device is positioned between the object and the image capturing device, and being positioned to reflect light at the first wavelength reflected by the object away from the image capturing device, and to transmit fluorescent light emitted from the foreign matter on the object to the image capturing device.

16. The system according to claim 12, wherein the device is a long pass filter.

17. The system according to claim 12, further comprising:
   a positioning device for automatically positioning one of i) the object, and ii) at least a portion of the image capture device, to a position for capturing the image of the at least the portion of the object and the foreign matter on the object.

18. The system according to claim 12, wherein the foreign matter is non-metallic.

19. An inspection system for semiconductor chip or semiconductor device packages, comprising:
   a light source for illuminating a semiconductor chip or semiconductor device package with excitation light, the excitation light from the light source having a first wavelength;
   an image capturing device;
   a filter device transmissive for light having a second wavelength which is different than the first wavelength, and reflective for light having the first wavelength, the light having the second wavelength being emitted from foreign non-metallic matter on the semiconductor chip or semiconductor device package, the image capturing device positioned to capture an image of at least a portion of the semiconductor chip or semiconductor device package and the foreign non-metallic matter using light transmitted through the filter device; and
   a processor configured to scan the image for defects including the foreign non-metallic matter on the semiconductor chip or semiconductor device package.

20. The inspection system according to claim 19, further comprising:
   a dark field illumination system providing dark field illumination of the semiconductor chip or semiconductor device package.

21. The inspection system 20, wherein the dark field illumination system includes a ring light.

22. The inspection system according to claim 20, wherein the dark field illumination system includes a diffuser.

23. The system according to 20, wherein the dark field illumination system illuminates the semiconductor chip or semiconductor device package with light at a third wavelength, and wherein the filter device is transmissive for light at the third wavelength reflected by the semiconductor chip or semiconductor device package.

24. The inspection system according to claim 19, further comprising:
   a processor controlling the light source and the dark field illumination system.

25. The inspection system according to claim 24, wherein the processor is configured to actuate both the light source and the dark field illumination system simultaneously.

26. The inspection system according to claim 24, wherein the processor is configured to actuate the light source and the dark field illumination system sequentially relative to one another.

27. The inspection system according to claim 19, further comprising:
   a positioning device moving the semiconductor chip or the semiconductor device package to a position for the illumination.

28. The inspection system according to claim 19, further comprising:
   a positioning device moving at least a portion of the image capture system relative to the device package to a position for capturing the image of the device package.

29. The system according to claim 19, wherein the filter device is positioned to reflect light at the first wavelength reflected by the semiconductor chip or semiconductor device package away from the image capturing device, and to transmit light at the second wavelength emitted by the foreign matter to the image capturing device.

30. A method of inspecting a semiconductor chip or semiconductor device package, comprising:
   illuminating a semiconductor chip or semiconductor device package with an excitation light, the excitation light at a first wavelength from the light source having a first wavelength;
   transmitting fluorescent light emitted from foreign non-metallic matter on the device package at a second wavelength to an image capturing device;
   directing light reflected from the semiconductor chip or semiconductor device package at the first wavelength away from the image capturing device;
   capturing a first image of the semiconductor chip or semiconductor device package using the fluorescent light; and
   identifying a presence of the foreign non-metallic matter on the semiconductor chip or semiconductor device package using the first image.

31. The method according to claim 30, further comprising:
   automatically positioning the semiconductor chip or semiconductor device package for the illumination.

32. A method of inspecting a semiconductor chip or semiconductor device, comprising:
   illuminating a semiconductor chip or semiconductor device package with an excitation light, the excitation light at a first wavelength from the light source having a first wavelength;
   transmitting fluorescent light emitted from foreign matter on the device package at a second wavelength to an image capturing device;
   directing light reflected from the semiconductor chip or semiconductor device package at the first wavelength away from the image capturing device;
   capturing a first image of the foreign matter on the semiconductor chip or semiconductor device package using the fluorescent light;
   illuminating the semiconductor chip or semiconductor device package with a light having a third wavelength different from the first wavelength;
   transmitting light reflected from the semiconductor chip or semiconductor device package at the third wavelength to the image capture device; and
   capturing a second image of the semiconductor chip or semiconductor device package using the light reflected from the semiconductor chip or semiconductor device package at the third wavelength.

33. A method of inspecting a semiconductor ship or semiconductor device, comprising:
   illuminating a semiconductor chip or semiconductor device package with an excitation light, the excitation light at a first wavelength from the light source having a first wavelength;
   transmitting fluorescent light emitted from foreign matter on the semiconductor chip or semiconductor device package at a second wavelength to an image capturing device;
   directing light reflected from the semiconductor chip or semiconductor device package at the first wavelength away from the image capturing device;
   capturing a first image of the foreign matter on the semiconductor chip or semiconductor device package using the fluorescent light;
   simultaneously with the step of illuminating the semiconductor chip or semiconductor device package with the light source, illuminating the semiconductor chip or semiconductor device package with a light having a third wavelength different from the first wavelength; and
   transmitting light reflected from the semiconductor chip or semiconductor device package at the third wavelength to the image capture device;
   wherein the first image is captured using the light reflected from the device package at the third wavelength.

34. A method of imaging an object, comprising:
   automatically positioning one of: i) the object, and ii) at least a portion of an image capturing device, in a first position;
   illuminating the object with excitation light, the excitation light having a first wavelength;
   transmitting fluorescent light emitted from foreign matter on the object at a second wavelength to the image capturing device;
   directing light reflected from the object at the first wavelength away from the image capturing device;
   capturing a first image of the foreign matter on the object using the fluorescent light;
   illuminating the object with a light having a third wavelength different from the first wavelength;
   transmitting light reflected from the object at the third wavelength to the image capture device;
   capturing a second image of the object using the light reflected from the object at the third wavelength; and
   repositioning the one of the object and the at least portion of the image capturing device, the repositioning occurring only after both the first image and the second image are captured.

35. The method according to claim 34, wherein the foreign matter is non-metallic, the method further comprising:
   identifying a presence of the foreign non-metallic matter on the object using the first image.

36. A method of imaging an object, comprising:
   a) illuminating an object with an excitation light having a first wavelength;
   b) transmitting fluorescent light emitted from foreign non-metallic matter on the object at a second wavelength to an image capturing device;
   c) simultaneously with step a), illuminating the object with light at a third wavelength using a dark field illumination system;

d) transmitting light reflected by the object at the second wavelength to the image capturing device;

e) directing light reflected from the object at the first wavelength away from the image capturing device;

f) capturing a first image of at least a portion of the object and the foreign non-metallic matter on the object using the fluorescent light and the light reflected at the second wavelength.

37. The method according to claim 36, further comprising:

automatically positioning one of: i) the object, and ii) at least a portion of the image capture device, to a first position so that the first image may be captured.

38. The method according to claim 36, wherein the foreign matter is non-metallic, the method further comprising:

identifying a presence of the foreign non-metallic matter on the object using the first image.

* * * * *